(12) United States Patent
Schlesinger et al.

(10) Patent No.: US 11,268,899 B2
(45) Date of Patent: Mar. 8, 2022

(54) PHOTOACOUSTIC METHOD WITH A MEASURING LIGHT HAVING A PREDETERMINED WAVELENGTH RANGE FOR THE DETERMINATION OF PROPERTIES OF AN INHOMOGENEOUS SAMPLE

(71) Applicant: HUMBOLDT-UNIVERSITÄT ZU BERLIN, Berlin (DE)

(72) Inventors: Raphael Schlesinger, Berlin (DE); Jan-Ferenc Kischkat, Berlin (DE); Hermann Von Lilienfeld-Toal, Gelnhausen (DE)

(73) Assignee: QUANTUNE TECHNOLOGIES GMBH, Berlin (DE)

( * ) Notice: Subject to any disclaimer, the term of this patent is extended or adjusted under 35 U.S.C. 154(b) by 0 days.

(21) Appl. No.: 16/756,348

(22) PCT Filed: Oct. 26, 2018

(86) PCT No.: PCT/EP2018/079400
§ 371 (c)(1),
(2) Date: Apr. 15, 2020

(87) PCT Pub. No.: WO2019/081704
PCT Pub. Date: May 2, 2019

(65) Prior Publication Data
US 2020/0326274 A1 Oct. 15, 2020

(30) Foreign Application Priority Data
Oct. 27, 2017 (EP) .................................... 17198860

(51) Int. Cl.
*G01N 21/17* (2006.01)
*A61B 5/145* (2006.01)
*A61B 5/00* (2006.01)

(52) U.S. Cl.
CPC ....... *G01N 21/1702* (2013.01); *A61B 5/0095* (2013.01); *A61B 5/14532* (2013.01); *G01N 2021/1706* (2013.01)

(58) Field of Classification Search
CPC ........ G01N 21/1702; G01N 2021/1706; A61B 5/14532; A61B 5/0095
See application file for complete search history.

(56) References Cited

U.S. PATENT DOCUMENTS 9,554,738 B1 * 1/2017 Gulati ................. A61B 5/0075
2010/0070233 A1 * 3/2010 Masumura ........... A61B 5/4312
702/127

OTHER PUBLICATIONS

Gao et al. "Single laser pulse generates dual photoacoustic signals for differential contrast photoacoustic imaging," Scientific Reports, Apr. 2017, vol. 7, No. 1, 626, 12 pages.

(Continued)

*Primary Examiner* — Dominic J Bologna
(74) *Attorney, Agent, or Firm* — Sheridan Ross P.C.

(57) ABSTRACT

A method comprises a) radiating at least one measurement light pulse having a pulse duration and intensity onto a measurement area of the inhomogeneous sample; b) detecting at least one pressure transient at the measurement area; and c) calculating a value for the energy density absorbed by the sample during the pulse duration from a curve of the at least one pressure transient at the start and at the end of the at least one measurement light pulse. The method further includes: repeating steps a) to c) for different angles of incidence of the measurement light; modelling the inhomogeneous sample as a stack of layers, each layer being assigned at least a layer thickness and an absorption coefficient, at least one absorption coefficient of a layer being a fitting parameter; and performing a fitting procedure for the fitting parameters; outputting the fitted fitting parameters.

10 Claims, 3 Drawing Sheets

(56) References Cited

OTHER PUBLICATIONS

Kottmann et al. "Glucose sensing in human epidermis using mid-infrared photoacoustic detection," Biomedical Optics Express, Apr. 2012, vol. 3, No. 4, pp. 667-680.
Translated International Search Report for International (PCT) Patent Application No. PT/EP2018/079400, dated Dec. 3, 2018, 2 pages.

* cited by examiner

PHOTOACOUSTIC METHOD WITH A MEASURING LIGHT HAVING A PREDETERMINED WAVELENGTH RANGE FOR THE DETERMINATION OF PROPERTIES OF AN INHOMOGENEOUS SAMPLE

CROSS REFERENCE TO RELATED APPLICATIONS

This application is a national stage application under 35 U.S.C. 371 and claims the benefit of PCT Application No. PCT/EP2018/079400 having an international filing date of 26 Oct. 2018, which designated the United States, which PCT application claimed the benefit of European Patent Application No. 17198860.3 filed 27 Oct. 2017, the disclosures of each of which are incorporated herein by reference in their entireties.

SUMMARY

The invention relates to a photoacoustic method for the determination of properties of an inhomogeneous sample with micrometre-scale depth resolution. The invention relates in particular to a photoacoustic method in which electromagnetic radiation is emitted into a surface of a sample and is absorbed by the sample while generating a pressure wave, wherein the pressure wave is propagated to the measurement area and is detected as a pressure transient.

The invention also relates to a photoacoustic method for the non-invasive determination of properties of living tissue, e.g. of living skin.

Photoacoustic measurement devices and sensors are known means for the detection and quantification of substances by their characteristic light absorption. In order to analyze a sample for a specific substance, the illumination of the sample occurs with a measuring light which has one or more optical wavelengths already known to be characteristic absorption wavelengths of the substance. The measuring light is irradiated in a pulsed manner into the sample and absorbed there locally to varying degrees depending on the distribution of the substance. The energy transmitted with the light absorption causes a heating and a thermomechanical expansion of the sample. Both trigger relaxation processes which distribute the inhomogeneously transmitted energy over the sample in order to re-establish the equilibrium. This occurs via thermal diffusion and the propagation of pressure waves—sonic waves—through the sample, inter alia up to the surface of the sample.

In established photoacoustic methods, the pressure waves are detected by piezoelectric sonic transducers as pressure transients at the surface of the sample. Such sonic transducers, in the following also referred to as detectors, can attain high temporal resolutions of typically a few tens of nanoseconds with corresponding electronic measurement equipment and are thus suitable for distinguishing between pressure-wave rise times from different depths of the sample. If the wavelength of the measuring light is chosen so that it is absorbed predominantly by localized substances or structures (e.g. haemoglobin in blood vessels) and if the pressure transient is detected simultaneously at a plurality of sites on the sample, then the sites of absorption can be identified and represented as a 3D image. For example, representations of blood vessel networks can be generated this way in vivo.

As a result of the high sonic velocity in solid or fluid samples, however, e.g. 1.5 µm/ns in water, conventional photoacoustics are only suitable for the analysis of a sample to a limited degree when the latter is irradiated with a measuring light that the sample has already completely absorbed at a depth of a few tens of micrometres under the sample surface. In these conditions, the pressure signal should be detected at the same measurement area in the surface into which the measuring light was previously irradiated, as absorption can practically only occur directly under the measurement area. The durations of the pressure signals arriving at the detector roughly at the same time are all correspondingly short. The limited time resolution of the detector generally does not allow a micrometre-scale resolution for the sample depths at which the pressure signals originate.

In the publication by Fei Gao et al., "Single laser pulse generated dual photoacoustic signals for differential contrast photoacoustic imaging", Scientific Reports |7: 626| DOI: 10.1038/s41598-017-00725-4 1, (2017), the use of long measuring light pulses is proposed in order to trigger two temporally separated pressure signals with every pulse, namely respectively one at the beginning and one at the end of a measuring light pulse. The two pressure signals belonging to a measuring light pulse have a non-linear correlation here. They have a fixed time interval and opposite polarity, but can possess different amplitudes depending on the duration of the measuring light pulse and the heating of the sample during the long pulse duration. Insights into the energy density deposited in the sample can thus be gained from the difference between the correlated pressure signals. The method of Fei Gao et al. shall be called differential photoacoustics (DPA) in the following.

For example, the following measurement task results from the paper by Kottmann et al., "Glucose sensing in human epidermis using mid-infrared photoacoustic detection", Vol. 3, No. 4/BIOMEDICAL OPTICS EXPRESS, S. 667 ff.: determining the blood sugar level in vivo by measuring the absorption of MIR measuring light with a wavelength of 10 µm in the "interstitial fluid" (ISF) below the approximately 20 µm thick stratum corneum (SC) of the living skin. According to this source, the measuring light is absorbed here within a depth range of up to 100 µm under the surface of the skin, and the absorption generates a pressure signal. The SC, however, does not provide any significant information regarding the blood sugar concentration per se. Only the absorption in layers lying deeper, in particular in the stratum spinosum, is suitable for inferring the glucose level. Identifying such varying properties of an inhomogeneous sample presupposes the attainment of a micrometre-scale depth resolution to a measurement depth of merely a few tens of micrometres under the surface.

Against this backdrop, there is an interest in a new photoacoustic measurement method, which can analyze inhomogeneous samples with a micrometre-scale depth resolution, specifically when the measuring light is from a spectral range which is readily absorbed by the inhomogeneous sample. To the knowledge of the inventors, differential photoacoustics has not yet been considered as a possible solution to this problem.

The invention aims to solve the object of proposing a photoacoustic method with a measuring light having a predetermined wavelength range for the determination of properties of an inhomogeneous sample, wherein the sample has an average absorption length from the interval 1-100 micrometres for the predetermined wavelength range.

The object is solved by means of a photoacoustic method with a measuring light having a predetermined wavelength range for the determination of properties of an inhomogeneous sample, wherein the sample has an average absorption length μ from the interval 1-100 micrometres for the predetermined wavelength range, comprising the steps:

a) irradiating a measurement area of the area F with $\sqrt{F} \gg \mu$ in the surface of the inhomogeneous sample with at least one measuring light pulse with a predetermined pulse duration and a predetermined intensity;

b) detecting at least one pressure transient at the measurement area, wherein the pressure transient results from the absorption of the at least one measuring light pulse in the inhomogeneous sample which generates a pressure wave propagating to the measurement area;

c) calculating a value for the energy density absorbed by the sample during the pulse duration from the curve of the at least one pressure transient at the beginning and at the end of the at least one measuring light pulse;

characterized by d) repeating steps a) to c) for different angles of incidence of the measuring light with respect to the normal of the measurement area, wherein the energy density values determined in c) are respectively indexed with the angle of incidence;

e) modelling the inhomogeneous sample as a stack of layers, wherein at least a layer thickness and an absorption coefficient are assigned to each layer, wherein at least one absorption coefficient of a layer is a fit parameter;

f) performing a fitting procedure for the fit parameters of the stack of layers, wherein the division of the energy density values indexed with the angle of incidence into contributions of the individual layers is varied by variation of the fit parameters until a predetermined consistency criterion is satisfied;

g) reading out the fitted fit parameters as values at least for the depth-resolved absorption coefficient of the inhomogeneous sample.

The dependent claims indicate advantageous embodiments of the method.

The photoacoustic method in accordance with the invention analyzes the time curve of detected pressure transients, yet abstains from any kind of assignment of sonic durations to sample depths. On the contrary, prominent structures of the pressure transients, which appear at the start and at the end of a measuring light pulse and which are called pressure pulses here, are registered temporally separated from one another and are, by way of example and preferentially, temporally integrated. The difference between the pressure pulse integrals, Δp, of a single pressure transient is the result of a different expansion response to the measuring light at the start and at the end of the long measuring light pulse. For example, an expansion of the sample generally occurs when the measuring light pulse arrives in the sample, and a contraction occurs as soon as the measuring light pulse ends, i.e. the light is turned off. During the duration of the measuring light pulse, electromagnetic energy is deposited in the sample, which leads to local heating. The temperature-dependent Grüneisen coefficient, Γ(T), of the illuminated volume of the sample is a defining parameter for the photoacoustic response and, in a first approximation, linearly dependent on the change in temperature:

$$\Gamma(T) = \Gamma_0 + \Gamma' \Delta T \quad (1)$$

The increase in temperature in the illuminated volume as a result of the absorbed radiation is determined at the same time by means of the thermal capacity $C_p$ of the sample. If these material coefficients are known for the sample under analysis or if one can make reasonable assumptions about them from knowledge of the sample, then the directly measured variable Δp can be converted into the energy deposited, ΔE, in relation to the illuminated volume, V, i.e. into the energy density absorbed:

$$\Delta p = \eta I_0 \delta t \times \frac{\Gamma'}{C_p} \times \frac{\Delta E}{V} \quad (2)$$

In equation (2) $I_0$ designates the measuring light intensity with which the sample is irradiated (in units power/area), St the rise or fall time of the measuring light pulse (cf. also FIG. 1) and η the efficiency of conversion of heat into pressure analogously to Fei Gao et al. (2017), divided by the sonic velocity and the detector-dependent integration time of the pressure transient.

The underlying idea of the invention is based on the insight that Δp exhibits a clear dependence on the angle of incidence, ϑ, of the measuring light in relation to the normal of the measurement area, specifically because it is posited that the measuring light is already heavily absorbed in the sample over short distances. At large angles, it no longer reaches layers lying deeper in the sample which it can still reach at a perpendicular incidence (ϑ=0°). A sequence of measurements of Δp(ϑ) at angles ϑ different from one another—synonymous with: respectively different by pairs—thus represents a set of linearly independent measurements of the sample from which information regarding the depth resolution of the sample can be extracted—then in fact necessarily on a micrometre scale.

The method in accordance with the invention slightly resembles a tomography, for example the CT scan, in which an object is thoroughly irradiated from different angles and imaged, and a computer model is accordingly reconstructed from the integrated view of the obtained images.

The invention must also carry out a reconstruction of the inhomogeneous sample, wherein this reconstruction can make the assumption, which significantly simplifies matters, that structural changes only occur along the depth axis. The inhomogeneous sample can then be modelled as a one-dimensional stack of layers comprising M number of layers, wherein M is a natural number. In accordance with the invention, each layer (with the index i=1, . . . , M) of the model is allocated at least a layer thickness, $d_i$, and an absorption coefficient, $\alpha_i$, as a property, wherein at least one absorption coefficient of a layer is provided as a fit parameter.

The sole directly angle-dependent variables on the right side of equation (2) are the energy deposited ΔE(ϑ) and the illuminated volume V(ϑ)=F×μ(ϑ), wherein F designates the area of the predetermined measurement area onto which the measuring light is irradiated and μ(ϑ) designates the depth of penetration of the radiation averaged over the sample. An implicit averaging of the photoacoustic response of the sample perpendicular to the depth axis, i.e. parallel to the sample surface, effectively already occurs because the dimensions of the measurement area, i.e. edge lengths or diameter respectively proportional to $\sqrt{F}$, are set so as to be very large in relation to μ.

The fact that the sample area actually illuminated can, as the result of refraction of the measuring light at an oblique incidence, also exhibit an edge area which does not lie under the measurement area is neglected here for simplification.

The distribution of the energy density deposited in the sample essentially depends on which path lengths the measuring light travels in which layers—under the effect of the relevant absorption coefficient. For example, at an angle of incidence close to 90°—grazing incidence—it is possible for the measuring light to be propagated and absorbed entirely in the uppermost layer of the sample. If the angle is reduced, the penetration depth changes and the measuring light can also be absorbed in a second or even a third layer, etc.

The change of the angle of incidence effectively amounts to the concurrent extension of all layer thicknesses of the model of the sample. In other words, it is sufficient to calculate for the layer model the light intensity I(x) with x as the depth axis from the model parameters and in the process to simply replace all $d_i$ with $d_i/\cos(\vartheta)$ for the different angles $\vartheta$. To clarify: a new calculation of the intensity I(x) is necessary for every variation of the layer thicknesses $d_i$ or of the angle $\vartheta$, as the intensity—and thus concurrently the measurable pressure response—changes even when solely the angle of incidence is varied.

With the help of the modelled light intensities, it is possible in accordance with the invention to apportion the absorbed energy density to the individual layers of the stack of layers, in other words to determine the contributions of the individual layers to the measured energy density. The following consideration serves this purpose:

The increase in the deposited energy over a depth interval, $\Delta x$, corresponds to the decrease in the irradiated power over the same interval multiplied by the duration of the measuring light pulse, $\Delta t$ (cf. FIG. 1). The measuring light intensity I(x) is the depth-dependent power area density, and $$\frac{\Delta E(x)}{\Delta x} \cong -F \times \Delta t \times \frac{dI(x)}{dx} \quad (3)$$

holds approximately true, although the difference quotient has been converted into a differential quotient on the right side for the purposes of simplification. The absorbed energy averaged over the entire penetration depth μ is obtained by a weighted integration $$\frac{\Delta E}{\mu} = \int_0^\mu \frac{\Delta E(x)}{\Delta x} \times \rho(x) dx \quad (4)$$

with weightings $$\rho(x) = \frac{I(x)}{\int_0^\infty I(x')dx'} \quad (5)$$

The weighting function in (5) is almost zero for x>μ, i.e. the upper integration limit in (4) can be set approximately to ∞. If (3) and (5) are inserted in (4) and one divides by the area F, this yields $$\frac{\Delta E}{V} = \frac{-\Delta t}{\int_0^\infty I(x')dx'} \times \int_0^\infty \frac{dI(x)}{dx} \times I(x) dx \quad (6)$$

$$\frac{\Delta E}{V} = \frac{\Delta t}{\int_0^\infty I(x')dx'} \times \sum_{i=1}^M \int_{d_{i-1}}^{d_i} \alpha_i \times I^2(x) dx \quad (7)$$

At the transition from (6) to (7), the sample is introduced as a stack of layers with M layers of layer thicknesses $d_i$,i=1, . . . , M with the definition $d_0$=0 as well as the absorption coefficient $\alpha_i$,i=1, . . . , M. In the individual layers, the intensity follows the known exponential curve, and respectively holds true $$\frac{dI(x)}{dx} = -\alpha_i \times I(x).$$

The dependence on the angle of incidence $\vartheta$ is suppressed in the equations up to this point. If it is now explicitly added, one obtains as a result:

$$\frac{\Delta E(\theta)}{F\mu(\theta)} = \frac{\Delta t}{\int_0^\infty I(\theta, x')dx'} \times \sum_{i=1}^M \int_{d_{i-1}/\cos\theta}^{d_i/\cos\theta} \alpha_i \times I^2(\theta, x) dx \quad (8)$$

Equation (8) is a conditional equation system for parameters defining the curve of the intensity I(x) in the stack of layers when $I_0$ is additionally known in advance. The left side of (8) represents measured values from the pressure transients evaluated in accordance with equation (2). Measurement values for in principle any number N of angles of incidence $\vartheta$ can be used in order to fill the equation system (8) with linearly independent equations.

It is ostensibly up to the user of the invention how the model of the inhomogeneous sample is to be configured and which parameters are to be selected as a priori unknown fit parameters. For example, layer thicknesses of a biological sample could be measured in advance by optical coherence tomography. The $d_1$,i=1, . . . , M would then be known and would thus no longer be fit parameters. It can be generally assumed that every layer of a stack of layers has at least one unknown fit parameter allocated to it. In accordance with the invention, an absorption coefficient is assigned to at least one layer as a fit parameter.

The number N of the angles of incidence considered in equation (8) should preferably correspond roughly to the number of unknown fit parameters in equation (8), which can be varied independently of one another. In accordance with the invention, at least two different angles of incidence should be used.

Checking and, if necessary, improving the assumption made during the framing of the equation (2) regarding the quotient $$\frac{\Gamma'}{C_p}$$

is incidentally also comprised by the invention. Indeed, the measured pressure response of the stack of layers is the sum of the pressure responses, $\Delta p_i$, of the individual layers, and each layer can have its own quotient $$\frac{\Gamma_i'}{C_p^i}$$

proportional to the $\Delta p_i$ assigned to it. This allows the establishment of a self-consistency loop, for example as follows:

a) Measure N pressure responses for N angles of incidence
b) Calculate N values for absorbed energy densities in accordance with equation (2)
c) Insert calculated energy densities in equation (8) and solve the equation system (generally numerically) for a model with M layers d) Allocate quotient $$\frac{\Gamma'_i}{C_p^i}$$

to the M layers and calculate a new average value $$\frac{\Gamma'}{C_p}$$

e) Repeat steps b) to d) until the parameters of the model no longer change

One typically interrupts self-consistency loops when the changes in the parameters between two successive runs fall within predetermined limits. In principle, it must always be the prerogative of the user of the method to formulate a specific consistency criterion, as only he/she knows the exact nature of the sample and his/her accuracy requirements for the parameters to be determined.

BRIEF DESCRIPTION OF THE FIGURES

The purpose of the following figures is the further clarification and the illustration of embodiments. The figures show.

DETAILED DESCRIPTION

Figure 1:
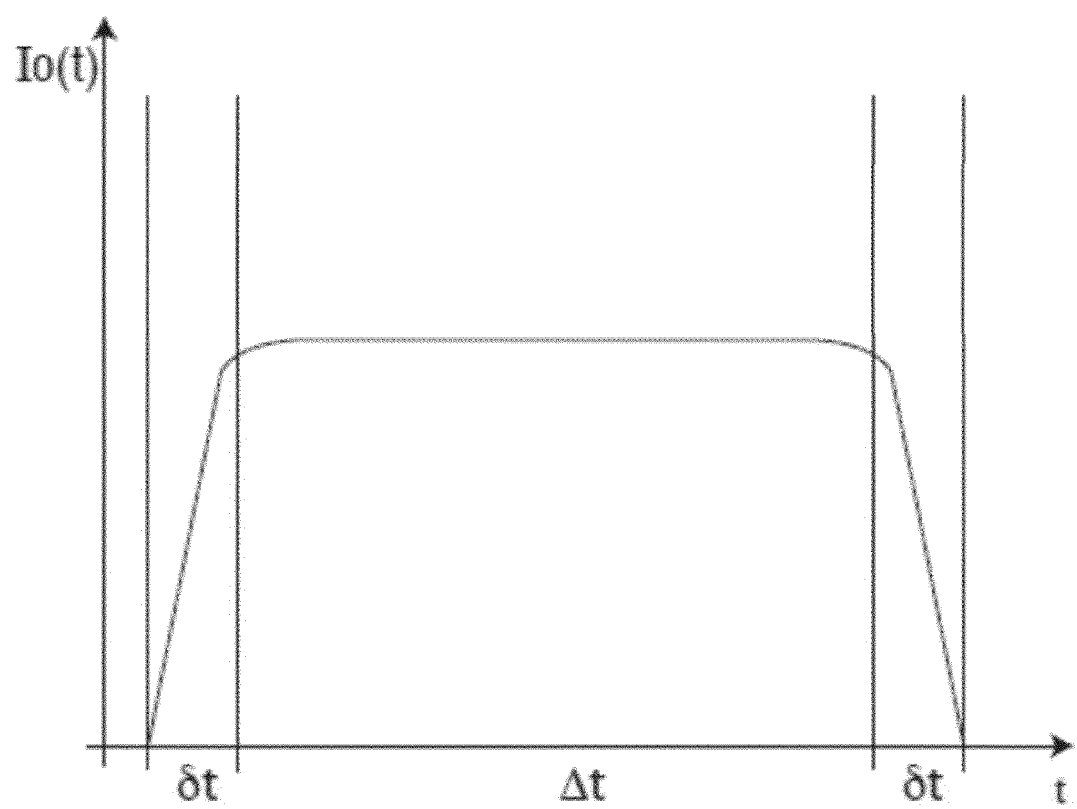
FIG. 1 a plot of the typical time curve of a measuring light pulse.

In FIG. 1, the time curve of a measuring light pulse is depicted illustratively. The intensity increases during a short time period St from 0 to its maximum value $I_0$, remains there for a time period $\Delta t \gg \delta t$, and subsequently falls during $\delta t$ back to 0. Pressure pulses by the expansion and contraction of the sample are respectively triggered during the rise or fall times of the measuring light pulses and generate the peaks in the measurable pressure transients during the time intervals of the length $\delta t$. The energy deposition and heating of the sample occurs during the pulse duration $\Delta t$. The pressure transients exhibit no appreciable structure in this phase. The pulse duration is preferably between 100 and 1000 nanoseconds, particularly preferably between 200 and 600 nanoseconds. By this means, it is ensured that the time interval between the two pressure pulses is so large that the first pulse can already have been registered—in any event has long since left the area of heating of the sample—before the second pulse is triggered. At the same time, the pulse duration is too small to allow a significant removal of the deposited energy by thermal diffusion between the trigger times of the pressure pulses.

The measuring light is irradiated onto a measurement area in the surface of the sample. The exact definition of the measurement area with regard to position, shape and surface area lies with the user. As a result of the assumed limited penetration depth of the measuring light in the sample, the strongest pressure response to the photoacoustic excitation is to be anticipated directly at the measurement area.

By way of example and preferentially, the irradiation of the measuring light can occur through a contact prism that is transparent for the measuring light. The contact prism has a sample contact surface onto which the measuring light is directed and which is located so as to be in mechanical contact with the sample. Pressure pulses generated by the measuring light penetrating the sample propagate up to the sample contact surface and can be captured there, for example by means of a sonic transducer (piezoelectric transducer), which is arranged on a detection surface of the contact prism opposite the sample contact surface. The pressure pulses thus have to travel an additional distance in the interior of the contact prism and arrive after a delay, which, however, is inconsequential for the evaluation according to the method in accordance with the invention. The sole purpose of the additional path is to avoid the blocking of the incidence of the measuring light onto the sample by the sonic transducer. In this respect, the measurement by means of a contact prism is considered a registration of the pressure transients at the measurement area—which is identical with the sample contact surface here.

Figure 2:
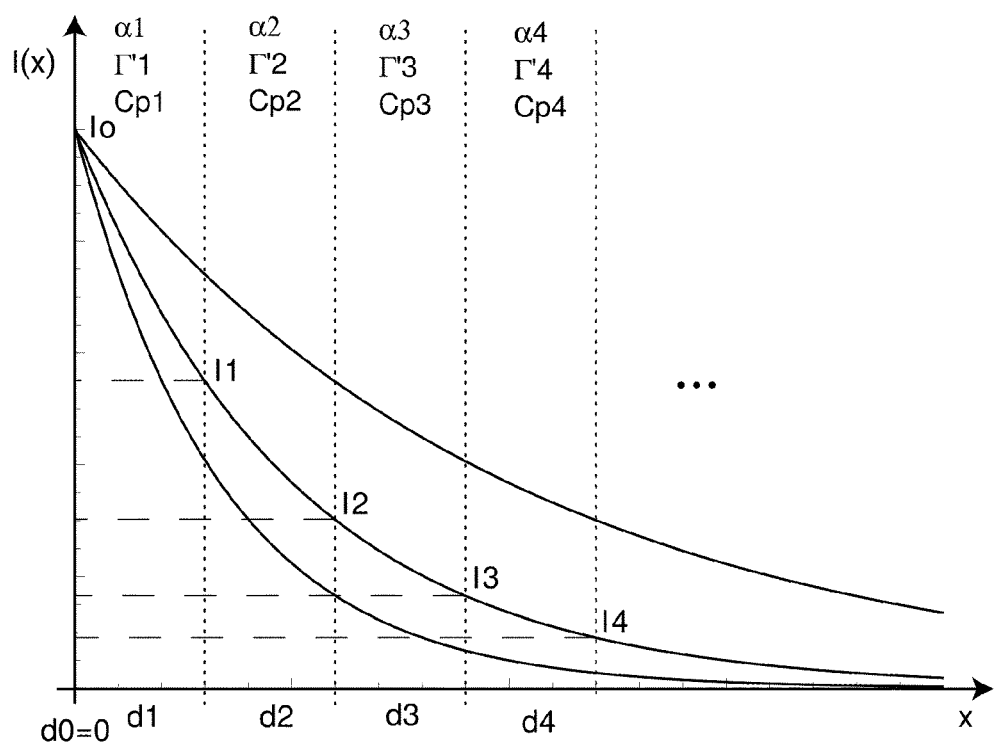
FIG. 2 a sketch of a layer model of the sample with the parameters assigned to the individual layers, and three intensity curves for different angles of incidence.

A model of the inhomogeneous sample as a stack of layers is depicted in FIG. 2. Layer thicknesses, absorption coefficients, Grüneisen coefficients and thermal capacities can be assigned to the individual layers. For the evaluation in accordance with the invention, however, only the temperature increase of the Grüneisen coefficient in relation to the thermal capacity is required, i.e. the quotient of the two. In this sense, only the quotients can indeed be used as fit parameters with the method, as already explained, for example when performing self-consistent loop calculations. The introduction of quotients of the temperature increase of the Grüneisen coefficient and the thermal capacity as fit parameters for the individual layers of the stack of layers is an advantageous embodiment of the method.

Which parameters are known and which have to be fitted basically depends on the nature of the sample and the previous knowledge of the user. Specifically for living biological samples, however, in particular for glucose determination in living skin, the absorption coefficient for the measuring light is of particular interest and typically changeable due to physiological processes and thus unknown. The invention thus aims to determine at least the depth-resolved absorption coefficient, $\alpha(x)$, of the inhomogeneous sample from pressure transients registered in an angle-dependent manner. This occurs approximatively by identifying $\alpha(x)$ with parameters $\alpha_i, i=1, \ldots, M$, which are constant by layer, of a layer stack model of the sample, wherein at least one $\alpha_i$ is unknown a priori and is determined by means of a fitting procedure. Generally, all $\alpha_i$ are unknown and act as fit parameters of the fitting procedure.

The layer thicknesses in FIG. 2 should preferably be selected from the range 500 nanometres to 100 micrometres. Layers substantially thinner than 500 nanometres will hardly exhibit sufficient linear absorption and thus no appreciable energy deposition. It is more expedient to model such thin layers in conjunction with a thicker adjacent layer. The method according to the invention, however, also expressly comprises the case of the—virtually trivial—model with merely exactly one layer. For it is proposed here also in this case to conduct at least two measurements of the pressure transients, consequently two measurements of the deposited energy density, at at least two different angles of incidence in order to determine the layer parameters. The fitting procedure in accordance with the invention for the fit parameters can naturally turn out to be quite simple in this case.

With the help of the three intensity curves in FIG. 2, the inventive idea can be illustrated once more with other words. The upper curve marks, for example, the intensity curve of the measuring light in the sample when the measuring light hits the measurement area perpendicularly ($\vartheta=0°$). The measuring light penetrates the furthest into and loses the least amount of power in the individual layers because it passes through each of the layers by the shortest route. The second curve from the top represents the intensity at an angle of incidence $\vartheta=\phi>0°$ and the bottom curve describes the intensity curve for the angle of incidence $\vartheta=\phi'>\phi$. As the angle of incidence increases, the measuring light transits each of the individual layers by a longer route so that the layers accumulate all the more energy density during the pulse duration, the closer they are to the measurement area. Deeper layers contribute increasingly less to nothing at all at large angles of incidence. In the integrated view of the angle-dependent pressure signals, the sequence and the properties of the layers can be inferred.

The indication of intermediate value intensities $I_1$, $I_2$, $I_3$, . . . at the middle curve should point to the fact that the integrals in equation (8) can all be solved analytically and lead here to precisely these intermediate values. It can be helpful to introduce these intermediate values as additional fit parameters and to solve the equation system with a larger number of angles of incidence. However, the intermediate values depend directly on the absorption coefficients and thicknesses of the layers so that then yet another consistency check has to be performed.

An advantageous option for also performing the fitting procedure for layer models with a plurality of individual layers and even a plurality of fit parameters per layer quickly and efficiently is available through a skillful use of the measured angle-dependent pressure transients or absorbed energy densities. If namely the measurement values are ordered according to angle of incidence and initially only subsets of the measurement values for angles of incidence $\vartheta>\vartheta_0>>0°$ are fed into the equation system (8)—i.e. the entire system is not evaluated—, then it is already possible to obtain reliable results for the fit parameters of the outermost layer(s). The used measurement values simply do not actually contain any contributions of deeper layers, i.e. this approach does not constitute an approximation, but merely includes an assumption regarding the penetration depth of the measuring light at the selected angles of incidence.

Should the assumption be grossly incorrect, i.e. if too few layers are provided for the selected subset of measurement values, then one initially obtains erroneous fit parameters, which, as more layers are subsequently added and a larger subset of the measurement values is used, again start to move in the direction of correct values. At the worst, computation time is wasted; however, one does not obtain an incorrect result.

However, if correct assumptions are made, the performance of the fitting procedure can be accelerated considerably, as the fit parameters of the stack of layers are preferably successively fitted for layers based on the outermost layer, wherein the satisfaction of the predetermined consistency criterion is checked repeatedly, beginning with the largest angle of incidence of the measuring light, for successively smaller angles of incidence. By fixing the parameters of the outer layers first and the deeper parameters bit by bit, it is possible to save computational work in the following steps of the fitting method, especially when a plurality of material variables are to be determined per layer as fit parameters.

It should be mentioned here that it is possible to make correct assumptions in the sense of the above statements in particular when a reiterative measurement task is to be solved invariably for the same sample for which one already possesses an established history of the possible variations of the fit parameters from previous measurements. This is especially the case with repeated glucose measurements on one subject.

As already stated, the method in accordance with the invention is very well suited for measurements on living biological samples, in particular on living skin samples. One goal is the non-invasive blood glucose determination in vivo on a human body part. For this goal, specifically the selection of mid-infrared (MIR) wavelengths for the measuring light is particularly suitable. The measuring light advantageously has wavelengths from the interval of 1 to 20 micrometres, particularly preferably from 6 to 12 micrometres.

It is obvious that it is possible to change the wavelength of the measuring light during the analysis of a single sample. For example, it is possible to run through a sequence of angles of incidence for a first wavelength and to register first angle-dependent pressure transients from the sample in order to subsequently use the same sequence of angles of incidence for a second wavelength for the measurement of a second sequence of pressure transients. This approach is particularly useful for the determination of absorption coefficients in accordance with the invention, as they typically depend on the wavelength. The spectral identification of specific substances occurs precisely by way of the wavelength dependence of absorption.

An advantageous embodiment of the invention is, however, found in the fact that the wavelength of the measuring light for predetermined angles of incidence is varied over an interval that is dependent on the angle of incidence. The main advantage here also lies in an acceleration of the analysis. When namely, using the example of glucose determination on living skin, the pressure transients for large angles of incidence—grazing incidence—are measured and values of the wavelength-dependent absorption coefficients are advantageously determined therefrom for epidermal layers, in particular for the stratum corneum and the stratum spinosum, then these measurement values are initially only meaningful for the outer stratum corneum. One knows in this context, however, from previous analyses that glucose is not an essential constituent of the stratum corneum. It is thus not necessary to irradiate a plurality of wavelengths which are particularly readily absorbed by glucose in order to verify an absorption coefficient in the outermost layer that in any case is only slightly variable. Only when the measuring light can also reach the stratum spinosum are glucose-sensitive wavelengths useful or important for the quantitative determination of the absorption in order for a realistic glucose concentration to be determinable. Consequently, it is sufficient to only irradiate such wavelengths at smaller angles of incidence of the measuring light.

Figure 3:
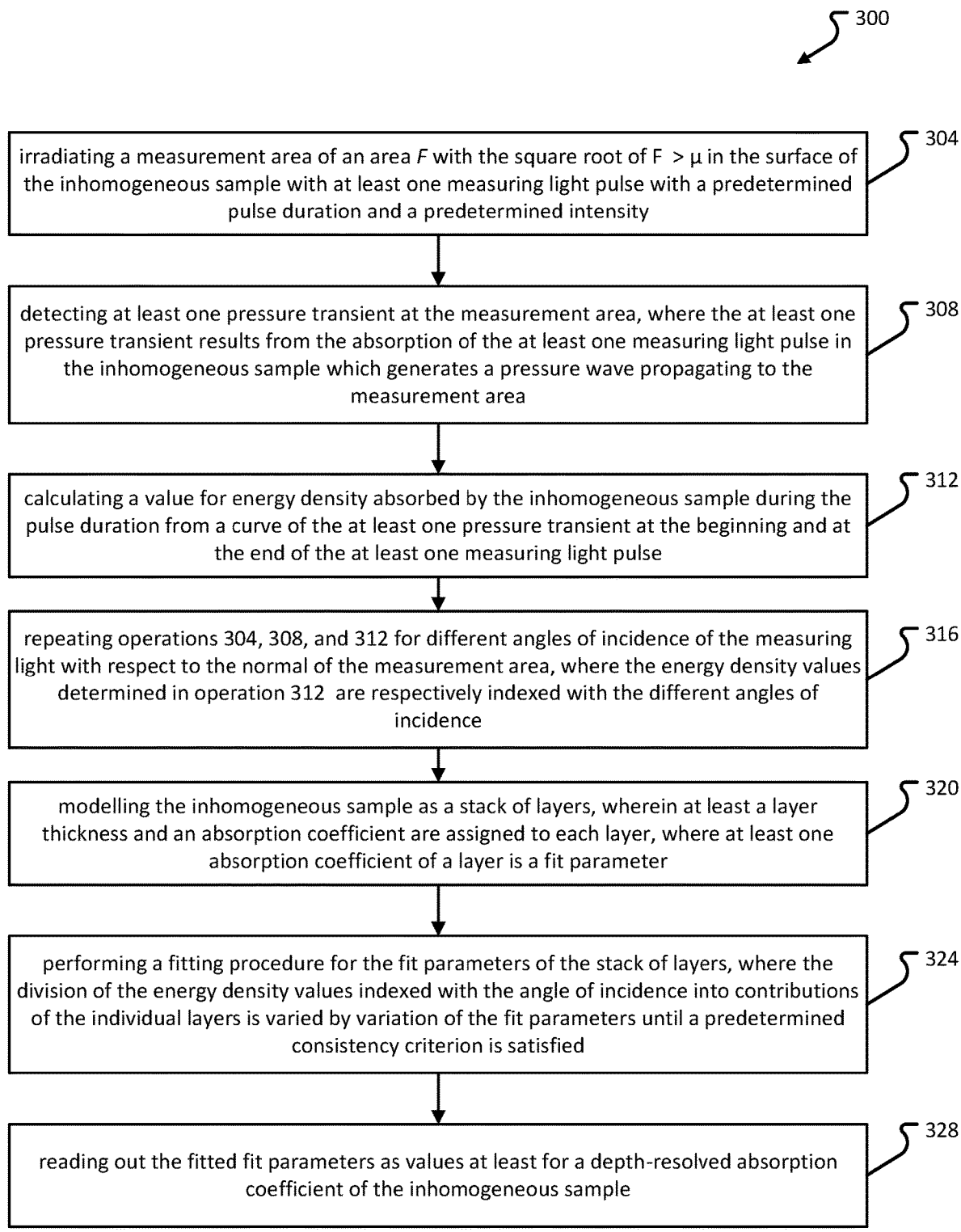
FIG. 3 a method according to at least one embodiment.

FIG. 3 illustrates a method 300 according to at least one embodiment. The method 300 may relate to a photoacoustic method with a measuring light having a predetermined wavelength range for the determination of properties of an inhomogeneous sample, where the inhomogeneous sample has an average absorption length $\mu$ from 1-100 micrometres for the predetermined wavelength range. Operation 304 includes irradiating a measurement area of an area F with the square root of $F>\mu$ in the surface of the inhomogeneous sample with at least one measuring light pulse with a predetermined pulse duration and a predetermined intensity.

Operation 308 includes detecting at least one pressure transient at the measurement area, where the at least one pressure transient results from the absorption of the at least one measuring light pulse in the inhomogeneous sample which generates a pressure wave propagating to the measurement area. Operation 312 includes calculating a value for energy density absorbed by the inhomogeneous sample during the pulse duration from a curve of the at least one pressure transient at the beginning and at the end of the at least one measuring light pulse. Operation 316 includes repeating operations 304, 308, and 312 for different angles of incidence of the measuring light with respect to the normal of the measurement area, where the energy density values determined in 312 are respectively indexed with the different angles of incidence. Operation 320 includes modelling the inhomogeneous sample as a stack of layers, wherein at least a layer thickness and an absorption coefficient are assigned to each layer, where at least one absorption coefficient of a layer is a fit parameter. Operation 324 includes performing a fitting procedure for the fit parameters of the stack of layers, where the division of the energy density values indexed with the angle of incidence into contributions of the individual layers is varied by variation of the fit parameters until a predetermined consistency criterion is satisfied. Operation 328 includes reading out the fitted fit parameters as values at least for a depth-resolved absorption coefficient of the inhomogeneous sample.

As a concluding remark, it should be pointed out that the modification of the angle of incidence during the illumination of the measurement area with measuring light can have the undesired side effect that the intensity actually irradiated into the sample varies, because a likewise variable part of the light is reflected by the sample. The reflected intensity can, however, be measured e.g. directly with a photodetector. By this means, a numerical correction factor for the intensities can be readily determined in the equations (2) and (8). It can, however, instead be advantageous to rather keep the actually penetrating measuring light intensity constant, as otherwise increased background noise is to be expected with the measured pressure transients. To this end, it is proposed to irradiate the measuring light onto the measurement area through an electronically switchable attenuating device, for example linearly polarized by a solenoid and a polarizer. By means of the selection of current supply to the coil, the polarization plane of the measuring light can be rotated so that optionally more or less measuring light reaches the measurement area. An automatable readjustment of the measuring light intensity can thus occur when, e.g. said photodetector continuously measures the reflected intensity and relays the same to a control unit for the coil current.

What is claimed is:

1. A photoacoustic method with a measuring light having a predetermined wavelength range for the determination of properties of an inhomogeneous sample, wherein the inhomogeneous sample has an average absorption length $\mu$ from 1-100 micrometres for the predetermined wavelength range, the method comprising:
   a) irradiating a measurement area of an area F with $\sqrt{F} \geq \mu$ in the surface of the inhomogeneous sample with at least one measuring light pulse with a predetermined pulse duration and a predetermined intensity;
   b) detecting at least one pressure transient at the measurement area, wherein the at least one pressure transient results from the absorption of the at least one measuring light pulse in the inhomogeneous sample which generates a pressure wave propagating to the measurement area;
   c) calculating a value for energy density absorbed by the inhomogeneous sample during the pulse duration from a curve of the at least one pressure transient at the beginning and at the end of the at least one measuring light pulse;
   d) repeating steps a) to c) for different angles of incidence of the measuring light with respect to the normal of the measurement area, wherein the energy density values determined in c) are respectively indexed with the different angles of incidence;
   e) modelling the inhomogeneous sample as a stack of layers, wherein at least a layer thickness and an absorption coefficient are assigned to each layer, wherein at least one absorption coefficient of a layer is a fit parameter;
   f) performing a fitting procedure for the fit parameters of the stack of layers, wherein the division of the energy density values indexed with the angle of incidence into contributions of the individual layers is varied by variation of the fit parameters until a predetermined consistency criterion is satisfied; and
   g) outputting the fitted fit parameters as values at least for a depth-resolved absorption coefficient of the inhomogeneous sample.

2. The photoacoustic method according to claim 1, wherein in step f), a quotient of a temperature derivation of a Grüneisen coefficient and thermal capacity of layer material are assigned as fit parameters to each layer.

3. The photoacoustic method according to claim 1, wherein the fit parameters of the stack of layers are successively fitted for layers based on the outermost layer, wherein the satisfaction of the predetermined consistency criterion is checked repeatedly, beginning with the largest angle of incidence of the measuring light, for successively smaller angles of incidence.

4. The photoacoustic method according to claim 1, wherein the pulse duration of the measuring light pulses is predetermined at a value from 100 to 1000 nanoseconds.

5. The photoacoustic method according to claim 4, wherein the inhomogeneous sample is a biological sample.

6. The photoacoustic method according to claim 5, wherein the wavelength of the measuring light for predetermined angles of incidence is varied over an interval that is dependent on the angle of incidence.

7. The photoacoustic method according to claim 5, wherein the biological sample includes epidermal layers including a stratum corneum and a stratum spinosum.

8. The photoacoustic method according to claim 1, wherein the stack of layers has individual layers with layer thicknesses from 500 nanometres to 100 micrometres.

9. The photoacoustic method according to claim 1, wherein the measuring light has wavelengths from 1 to 20 micrometres.

10. A photoacoustic method with a measuring light having a predetermined wavelength range for the determination of properties of an inhomogeneous sample, wherein the inhomogeneous sample has an average absorption length $\mu$ from 1-100 micrometres for the predetermined wavelength range, the method comprising:
    a) irradiating a measurement area of an area F with $\sqrt{F} \geq \mu$ in the surface of the inhomogeneous sample with at least one measuring light pulse with a predetermined pulse duration and a predetermined intensity;

b) detecting at least one pressure transient at the measurement area, wherein the at least one pressure transient results from the absorption of the at least one measuring light pulse in the inhomogeneous sample which generates a pressure wave propagating to the measurement area;

c) calculating a value for energy density absorbed by the inhomogeneous sample during the pulse duration from a curve of the at least one pressure transient at the beginning and at the end of the at least one measuring light pulse;

d) repeating steps a) to c) for different angles of incidence of the measuring light with respect to the normal of the measurement area, wherein the energy density values determined in c) are respectively indexed with the different angles of incidence;

e) modelling the inhomogeneous sample as a stack of layers, wherein at least a layer thickness and an absorption coefficient are assigned to each layer, wherein at least one absorption coefficient of a layer is a fit parameter;

f) performing a fitting procedure for the fit parameters of the stack of layers, wherein the division of the energy density values indexed with the angle of incidence into contributions of the individual layers is varied by variation of the fit parameters until a predetermined consistency criterion is satisfied, wherein a quotient of a temperature derivation of a Grüneisen coefficient and thermal capacity of layer material are assigned as fit parameters to each layer; and g) outputting the fitted fit parameters as values at least for a depth-resolved absorption coefficient of the inhomogeneous sample; wherein:

the fit parameters of the stack of layers are successively fitted for layers based on the outermost layer, the satisfaction of the predetermined consistency criterion is checked repeatedly, beginning with the largest angle of incidence of the measuring light, for successively smaller angles of incidence, the pulse duration of the measuring light pulses is predetermined at a value from 100 to 1000 nanoseconds, the stack of layers has individual layers with layer thicknesses from 500 nanometres to 100 micrometres, the inhomogeneous sample is a biological sample including epidermal layers, the measuring light has wavelengths from the interval 1 to 20 micrometres, and the wavelength of the measuring light for predetermined angles of incidence is varied over an interval that is dependent on the angle of incidence.

* * * * *